(12) United States Patent
Meredith

(10) Patent No.: US 6,755,365 B1
(45) Date of Patent: Jun. 29, 2004

(54) AUTOMATED BONE GRINDER

(76) Inventor: Thomas L. Meredith, 6524 Bansbury Crossing, Brentwood, TN (US) 37027

( * ) Notice: Subject to any disclaimer, the term of this patent is extended or adjusted under 35 U.S.C. 154(b) by 150 days.

(21) Appl. No.: 10/062,285

(22) Filed: Feb. 1, 2002

(51) Int. Cl.[7] .............................................. B02C 19/12
(52) U.S. Cl. ......................... 241/29; 241/15.2; 241/236
(58) Field of Search ........................... 241/30, 29, 236, 241/152.2

(56) References Cited

U.S. PATENT DOCUMENTS

| | | | |
|---|---|---|---|
| 5,607,269 A | | 3/1997 | Dowd et al. ................. 409/134 |
| 5,906,322 A | * | 5/1999 | Hama ....................... 241/152.2 |
| 5,918,821 A | * | 7/1999 | Grooms et al. ................ 241/27 |
| 6,162,227 A | | 12/2000 | Eckhardt et al. .............. 606/84 |
| 6,287,312 B1 | | 9/2001 | Clokie et al. ................. 606/85 |
| 6,402,070 B1 | * | 6/2002 | Ishida et al. ................ 241/236 |

OTHER PUBLICATIONS

Thomas Matthew Industries, Inc. brochure for Model ABG04, including a picture the single internal cutting element. This model was sold as early as 1992.

* cited by examiner

*Primary Examiner*—Mark Rosenbaum
(74) *Attorney, Agent, or Firm*—Waddey & Patterson, P.C.; Phillip E. Walker; Mark J. Patterson

(57) ABSTRACT

The present invention provides a bone grinding apparatus, which comprises a grinding chamber, primary and secondary cutting elements positioned within the grinding chamber to sequentially perform primary and secondary cutting operations on the bone, and a drive mechanism operatively engaging the primary and secondary cutting elements. The apparatus also includes a bone supplying cylinder engaging the grinding chamber and adapted to transport the bone to the cutting elements at a consistent pressure. The apparatus also includes a sealing component designed to operatively engage the drive mechanism and to separate the drive mechanism from the cutting elements.

33 Claims, 9 Drawing Sheets

AUTOMATED BONE GRINDER

BACKGROUND OF THE INVENTION

1. Field of the Invention

The present invention relates generally to a bone grinding apparatus adapted to automatically cut bone into bone tissue powder for application in medical procedures.

2. Description of the Prior Art

Numerous medical procedures require the donation of human organs and tissues. Bone is one of the required human tissues needed for many of these medical procedures. Among other uses, donated bone samples are used as adhesives and grafting material in bone grafting operations, as protective layers in prosthetic implants, and as bone tissue composites in the creation of screws, disks, plates, pins, and joint sockets used in corrective surgeries. Regardless of the ultimate form in which donated bone is used, donated bone samples must first be processed by a grinding apparatus into bone tissue powder. The bone tissue powder is then demineralized and used in the previously mentioned capacities to facilitate the medical operation.

Several attempts have been made to create devices that correctly mill the bone samples into a useable powder form. Numerous issues have arisen that have complicated this process. First of all, conventional bone grinding systems require a two stage milling operation using separate pieces of equipment. These prior art devices lack the ability to transform the donated sample directly into bone tissue powder. This requires the bone to be ground first into intermediary pieces within one grinding apparatus, and then the pieces must be physically transferred to a second apparatus that then converts the pieces into the bone tissue powder form required in medical procedures. Since these prior art devices require multiple pieces of equipment, which necessitates a transfer of the bone specimen between the pieces of equipment, these prior art devices fail to adequately and efficiently transform the precious gift of human bone into the needed bone tissue powder.

A second drawback of conventional bone grinding systems is the likelihood of contamination of the bone sample during the grinding process. Throughout the grinding process, the bone sample must remain in a sterile environment. Conventional bone grinding devices fail to adequately protect that sterile environment due to the drive portion of these devices being physically located in the same area as the dispensing portion. For example, Grooms U.S. Pat. No. 5,918,821 has the motor portion of the grinding apparatus in close proximity to the dispensing portion. Thus, numerous samples of bone tissue run a high risk of contamination during the operation of the Grooms' apparatus. Also, any maintenance or repair work on any portion of the Grooms' grinding apparatus requires the entire apparatus be removed from the surgical environment in order to maintain a sterile medical facility. Therefore, the Groom's patent fails to adequately prevent the contamination of bone tissue, which is detrimental to the sterility requirement of bone tissue powder in medical applications.

Attempts to alleviate this contamination issue have been unsuccessful in the past. For example, Dowd U.S. Pat. No. 5,607,269 discloses a bone grinding apparatus that has its drive system enclosed in a box. This box initially separates the drive portion of the grinding apparatus from the location where the bone is processed. However, once the bone has been processed, the Dowd invention still requires the bone to be brought through the same environment that contains the drive mechanism before the ground bone is used for its medical purpose. Therefore, the Dowd patent fails to address the contamination issues associated with the processed bone and the drive mechanism for the grinding apparatus sharing the same surgical environment.

Another problem associated with grinding bone into usable bone tissue powder is the breakdown of morphogenetic proteins, which leads to a reduction in osteoinductivity. Osteoinductivity is a characteristic of bone tissue powder necessary to make the bone tissue powder useful within the human body. Morphogenetic proteins are the main element within the bone that maintains osteoinductivity. The major enemy to the morphogenetic proteins is the heat produced during the grinding process. The heat produced in most grinding devices is unchecked due to the lack of a controlled automated process that regulates the speed of the cutting elements and the pressure and rate at which the bone sample is fed to the cutting elements.

For example, the Grooms patent requires a human user to manually press on a plunger in order to supply the bone to its grinding elements. This manual process fails to maintain a consistent pressure or speed with which the bone sample is supplied to these grinding elements.

The Dowd apparatus also fails to maintain a consistent pressure or speed of the bone sample during the grinding process. The Dowd patent uses a holding vice to support the bone sample as a drill bit shaves off bone particles. The processing portion of the Dowd apparatus is not pressurized and lacks the controlled environment necessary in creating a consistent pressure and speed of the bone sample supplied to the grinding element. Thus, the Dowd device also fails to efficiently maintain the Osteoinductive characteristic of the bone sample used in the grinding process.

Thus, there is a need for an automated bone grinding apparatus adapted to sterilely process bone into bone tissue powder for use in medical procedures.

SUMMARY OF THE INVENTION

The present invention provides a bone grinding apparatus, which comprises a grinding chamber, primary and secondary cutting elements positioned within the grinding chamber to sequentially perform primary and secondary cutting operations on the bone, and a drive mechanism operatively engaging the primary and secondary cutting elements. The apparatus also includes a bone supplying cylinder engaging the grinding chamber and adapted to transport the bone to the cutting elements at a consistent pressure. A sealing component operatively engages the drive mechanism and separates the drive mechanism from the cutting elements.

A method for grinding bone is also disclosed. This method includes the steps of providing a sequentially arranged plurality of cutting tools and rotating a first cutting tool and a second cutting tool in the same direction, thereby creating a shearing action between the first cutting tool and the second cutting tool. The method also teaches supplying a bone sample to the cutting tools and dispensing that sample in bone tissue powder form.

A main purpose of this bone grinding apparatus is to efficiently and effectively convert human cortical bone into bone tissue powder for use in many medical procedures. In order to arrive at the bone tissue powder, an apparatus and method for efficiently and effectively cutting donated human cortical bone into the bone tissue powder is required. Key characteristics of any apparatus and method that would effectively and efficiently process human cortical bone into bone tissue powder would include automation, sterilization, and retention of the osteoinductivity of the bone during the conversion process. Also, it is extremely important not to waste any of the donated human cortical bone during the cutting process, due to the limited supplies of suitable bone available for conversion into bone tissue powder.

It is therefore a general objective of the present invention to provide a bone grinding apparatus designed to convert bone into bone tissue powder.

Another objective of the present invention is to provide a bone grinding apparatus that converts human cortical bone into bone powdered tissue and retains the osteoinductive characteristic of the bone.

Still another object of this invention is to automate the process of converting bone into bone tissue powder.

Still yet another object of the present invention is the efficient collection and dispersion of bone tissue powder once the bone sample has been processed into said powder.

Another object of the present invention is to environmentally separate the driving mechanism of a bone grinding apparatus from the other portions of the bone grinding apparatus that come in contact, or in close proximity, with the bone sample or bone tissue powder during the conversion process.

Still yet another object of the present invention is the combination into one grinding apparatus all required steps to reduce human cortical bone into bone tissue powder.

Numerous other objects, features and advantages of the present invention will be readily apparent to those skilled in the art, upon the reading of the following disclosure, when taken in conjunction with the new drawings.

BRIEF DESCRIPTION OF THE DRAWINGS

FIG. 4 shows the top of the bone supplying cylinder open to allow entry of the bone sample that is to be cut into bone tissue powder.

DETAILED DESCRIPTION OF THE PREFERRED EMBODIMENTS

Figure 1:
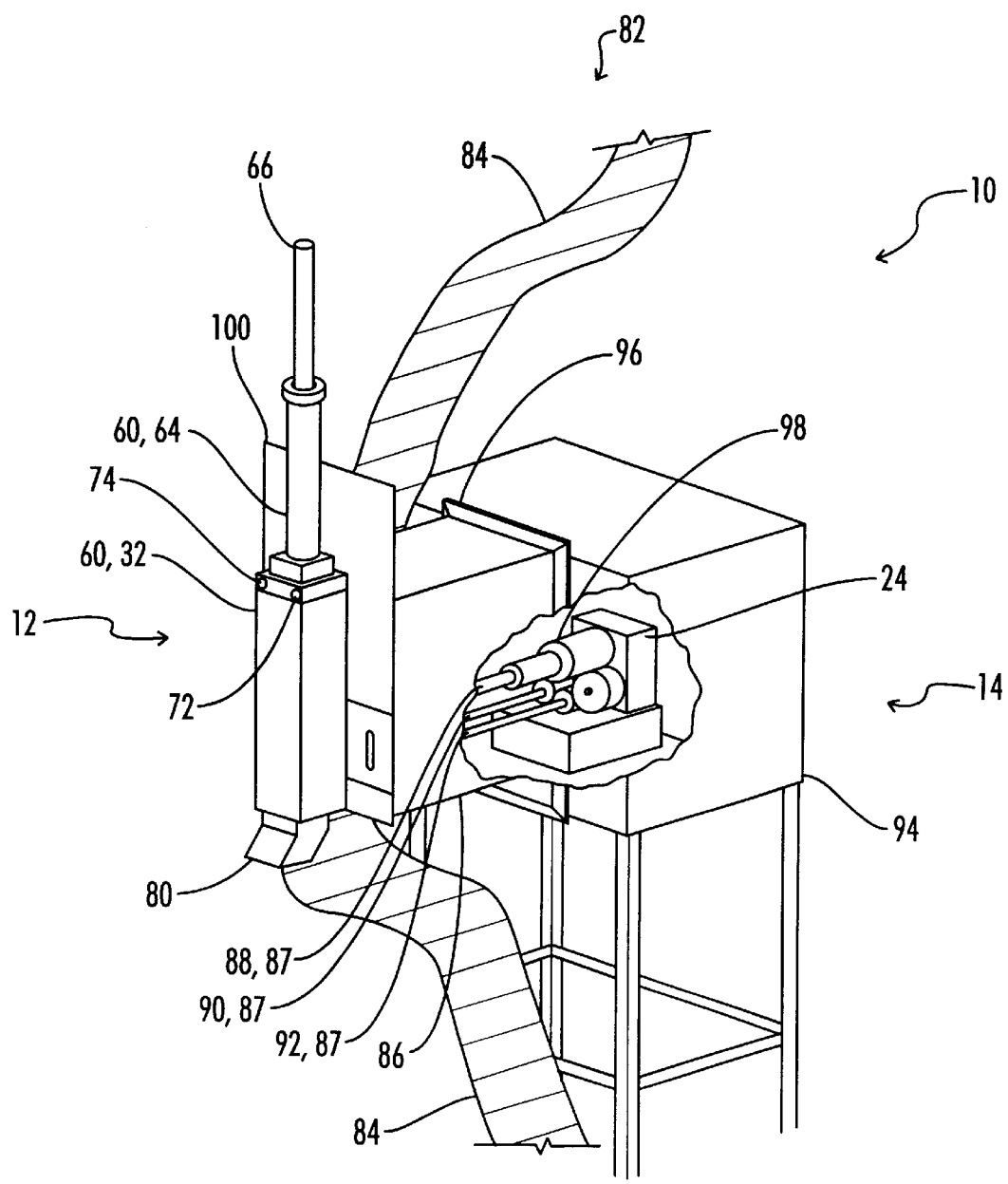
FIG. 1 is a perspective view of the bone grinding apparatus shown with a portion of the wall and control box removed.
Figure 2:
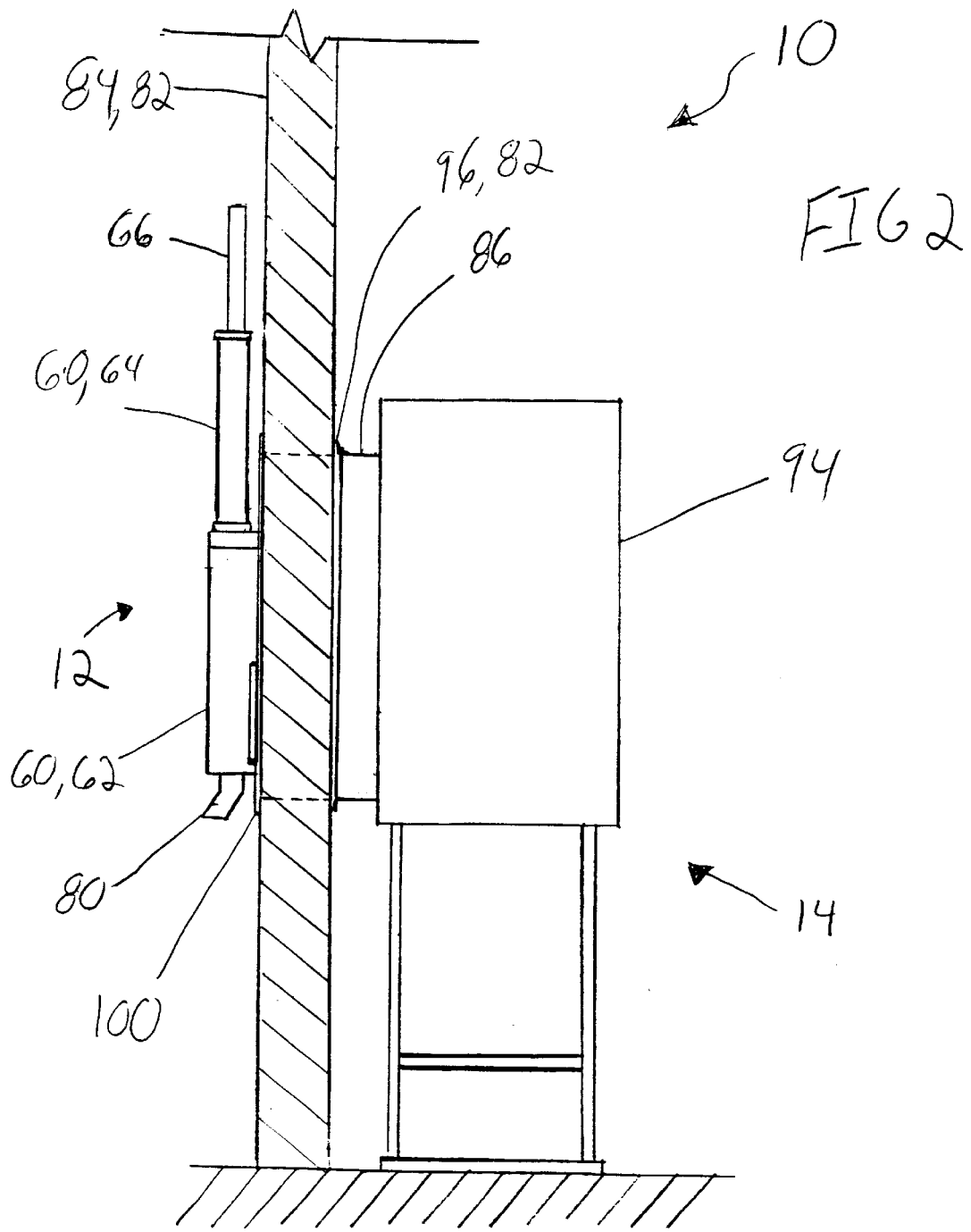
FIG. 2 is a side elevation view of the bone grinding apparatus.

Referring now to FIG. 1, the bone grinding apparatus of the present invention is shown and is generally designated by the numeral 10. The bone grinding apparatus 10 can be described as having two sections, the processing section 12 and the drive section 14, respectively. The processing section 12 includes the grinding chamber 16 and a plurality of cutting elements 17. The grinding chamber 16 includes the area encompassing the cutting elements 17 in which the bone 22 engages the cutting element 17. The bone drive section 14 includes a drive mechanism 24 operatively engaging the plurality of cutting elements 17.

Figure 3:
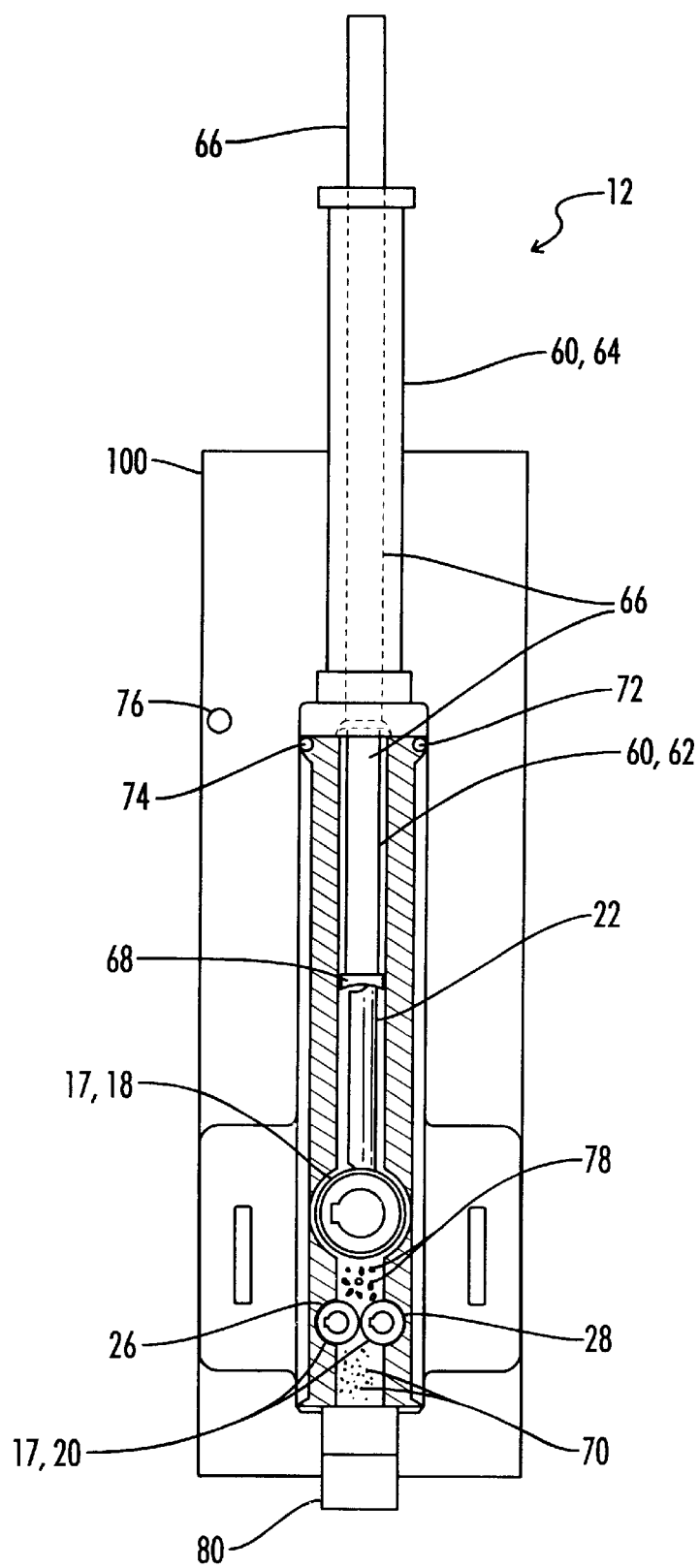
FIG. 3 is a front elevation view of the processing section of the bone grinding apparatus. This view shows the front cover plate removed, allowing a view of the relationship between the grinding elements, guide chute, and discharge path during operation of the apparatus.

As seen in FIG. 3, the cutting elements 17 include a primary cutting element 18 and a secondary cutting element 20, which can also be described as the first cutting element 18 and the second cutting element 20, respectively. The primary cutting element 18 and secondary cutting element 20 are positioned within the grinding chamber 16 to sequentially perform primary and secondary cutting operations on the bone 22. This positioning allows the bone 22 to cycle through a single processing apparatus creating bone tissue powder 70 that is suitable for medical applications.

Figure 4:
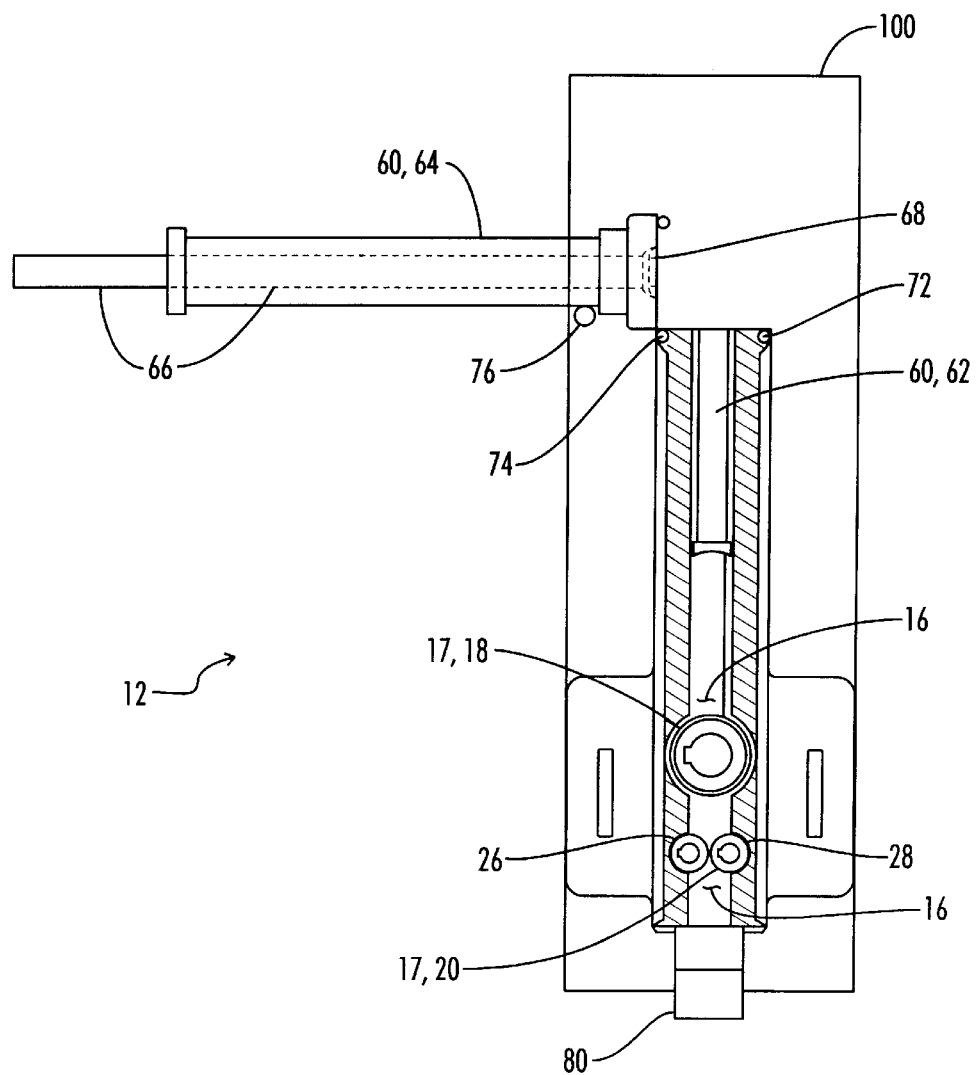
FIG. 4 is a front elevation view similar to FIG. 3.
Figure 5:
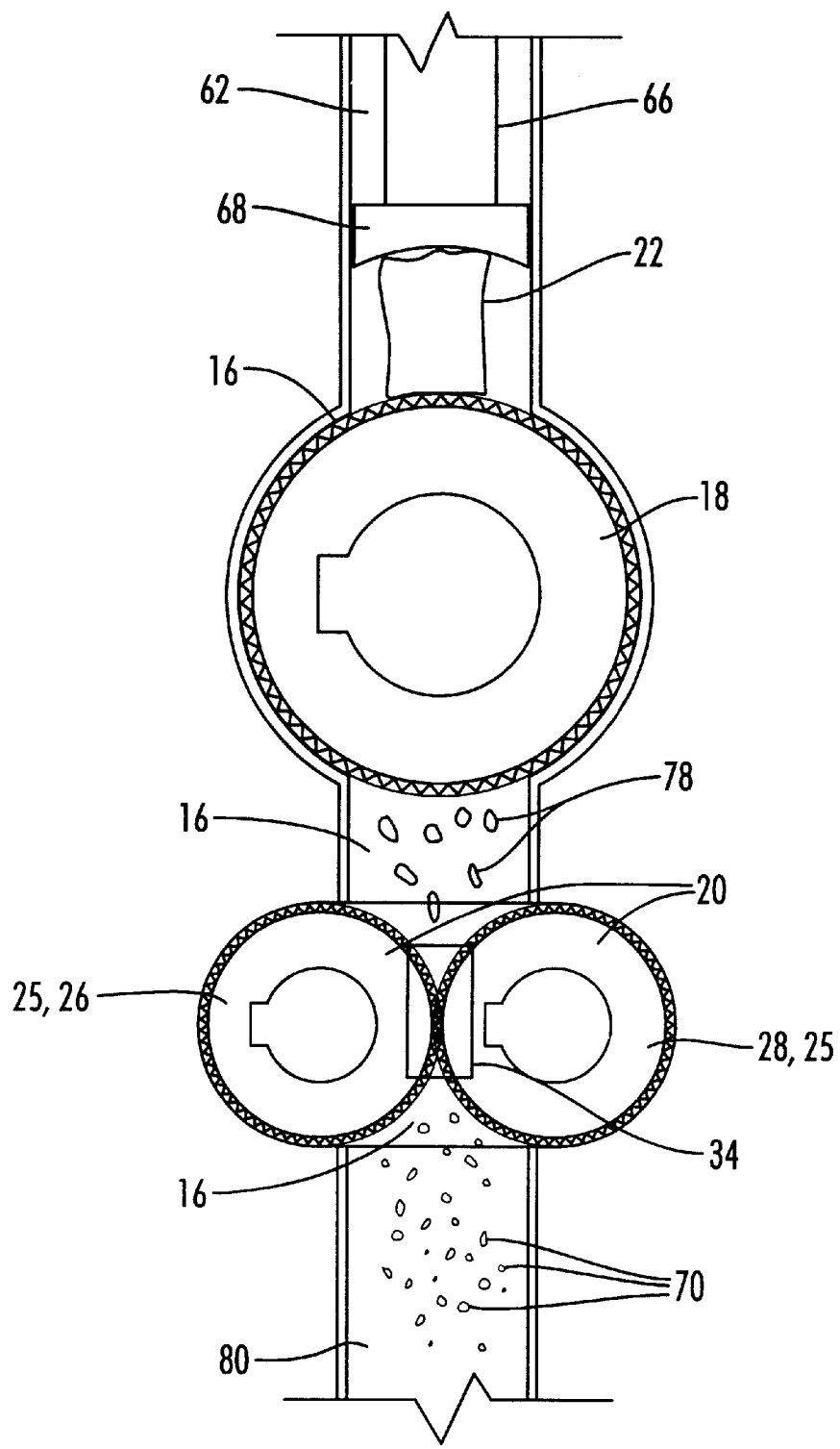
FIG. 5 is a detailed view of the cutting elements. This view shows the bone engaging both the primary and secondary cutting elements as the bone is processed from its natural state into the bone tissue powder.

As seen in FIGS. 3, 4, and 5, the secondary cutting element 20 comprises a plurality of cutting tools 25. The plurality of cutting tools 25 includes a first cutting tool 26 and a second cutting tool 28. The first cutting tool 26 includes a first set of teeth 30, while the second cutting tool 28 includes a second set of teeth 32. The first cutting tool 26 and the second cutting tool 28 are positioned in an opposed relationship within the grinding chamber 16 to define a cutting zone 34 between the first set of teeth 30 and the second set of teeth 32. A drive mechanism 24 moves the first set of teeth 30 in a first direction 36 through the cutting zone 34 and the second set of teeth 32 in an opposite direction 38 through the cutting zone 34, whereby the current movement of the first set of teeth 30 and the second set of teeth 32 will apply shear forces to the bone 22 located in the cutting zone 34.

Figure 6:
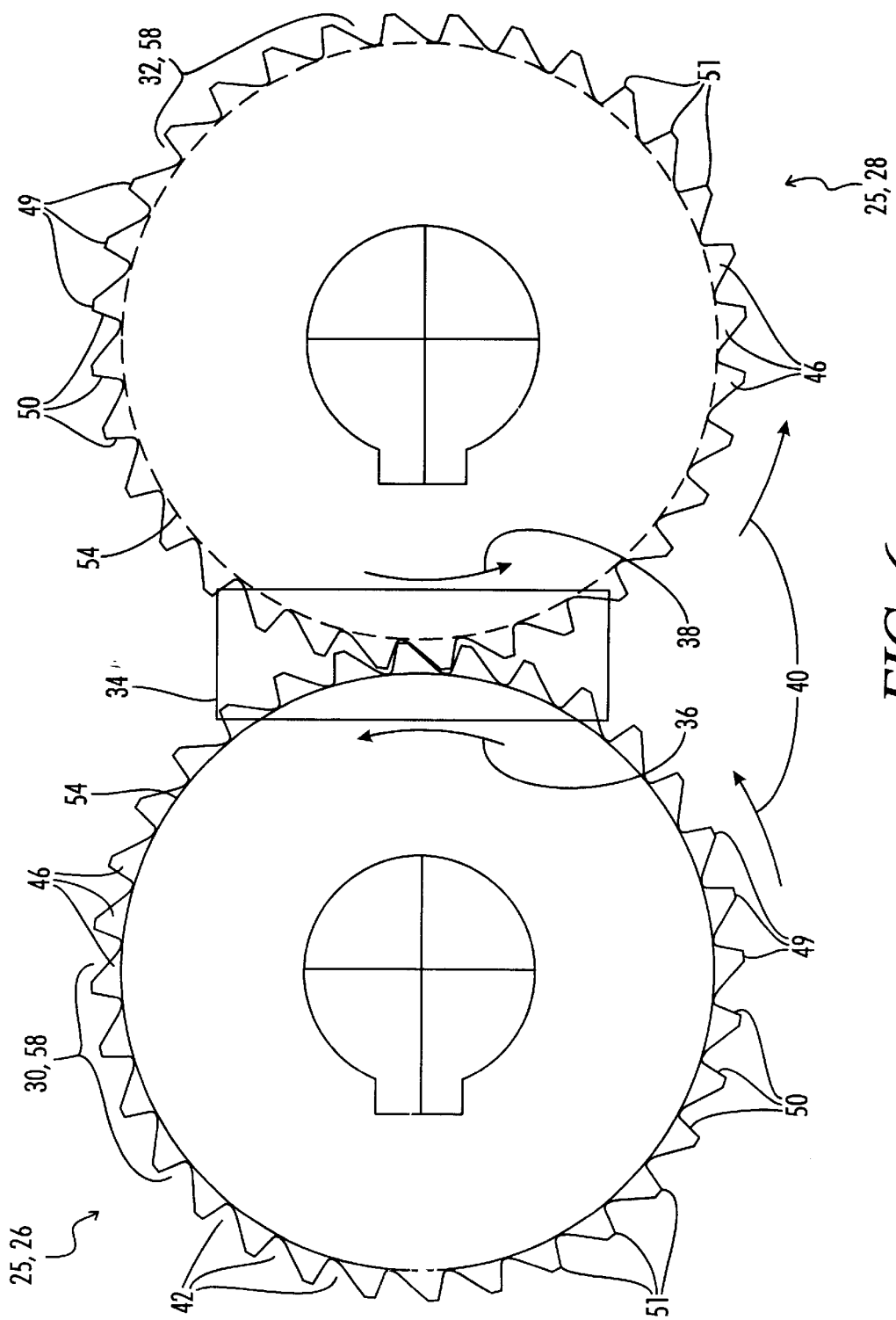
FIG. 6 is a detailed frontal view of the interaction between the cutting tools of the secondary cutting element.
Figure 7:
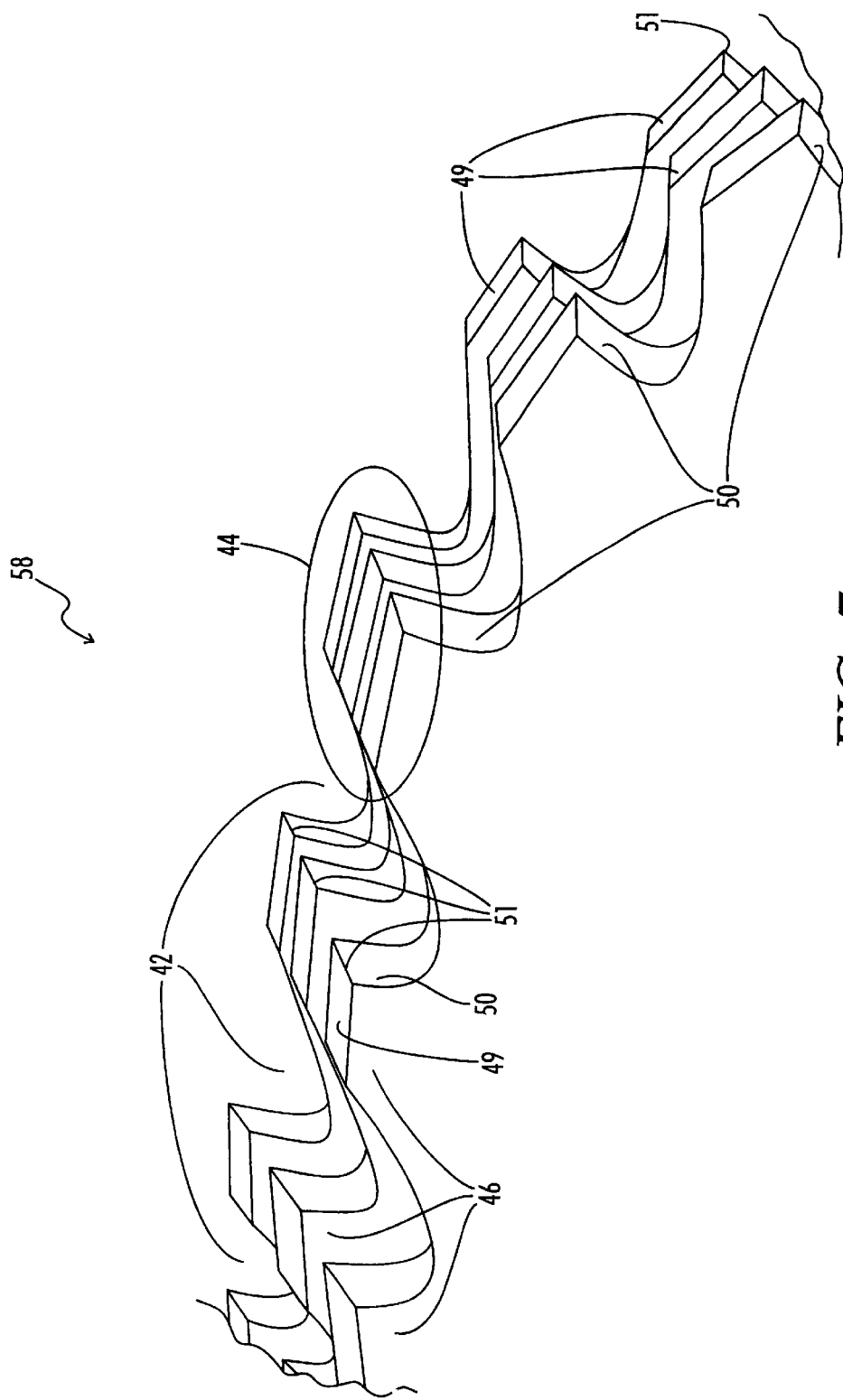
FIG. 7 is a side perspective view of a portion of one of the cutting tools of the secondary cutting element.

In a preferred embodiment, the drive mechanism 24 concurrently rotates the first cutting tool 26 and the second cutting tool 28 in the same direction 40, whereby the first set of teeth 30 and the second set of 32 apply shear forces to the bone 22 located in the cutting zone 34. As seen in FIG. 6, the first set of teeth 30 is positioned within the cutting zone 34 to alternate with and partially overlap the second set of teeth 32.

The first cutting tool 26 and the second cutting tool 28 rotate in the same direction 40. This allows the first cutting tool 26 to cut the bone 22 using the second cutting tool 28 as its opposing shear force. The second cutting tool 28 then completes a portion of a rotation during which it cleans the first cutting tool 26 of any bone fragments 22.

The first set of teeth 30 of the first cutting tool 26 and the second set of teeth 32 of the second cutting tool 28 each contain individual teeth 46. Each tooth 46 in each set of teeth 30 and 32 includes a cutting edge 51. The cutting edge 51 is created by the positioning of the tooth face 50 and the top surface 49. The tooth face 50 extends radially from the circumference 54 of each cutting element 17. The top surface 49 is positioned to be substantially perpendicular to the tooth face 50 to create a cutting edge 51. The angle defined by an intersection between the top surface 49 and the tooth face 50 can preferably vary in a range of 80 to 100 degrees, but is most preferably at 90 degrees.

The cutting edge 51 is instrumental in processing the bone 22 into bone tissue powder 70. By design, the cutting edge 51 is the portion of each tooth 46 that initially engages the bone 22 during the cutting process. This is due to the fact that the positioning of both the tooth face 50 perpendicular to the circumference 54 and the top surface 49 parallel to the circumference 54 of each cutting element 17 allows the cutting edge 51, which is the intersection of the tooth face 50 and the top surface 49, to engage the bone as each cutting element 17 rotates about its axis 55. As a result, the cutting edge 51 is the portion of each individual tooth 46 in each set of teeth 58 that cuts the bone 22. Hence, the size and shape of the top surface 49 and the tooth face 50, which comprise the cutting edge 51, become critical in determining the desired particle size of bone tissue powder 70. Current medical technology requires this micron particle size for the bone tissue powder 70 to be between 125 and 850 microns.

In alternate embodiments of the bone grinding apparatus 10, the cutting elements 17 can be replaced with appropriate sized alternate cutting elements 17 to provide variations in the micron size of particles as needed to fulfill other bone tissue powder 70 requirements. Variation in the cutting element 17 also allows the bone grinding apparatus 10 to cut other items, including, but not limited to, animal bone and other forms of tissue.

This design of the cutting tools 25 allows the cutting tools 25 to physically shear the bone 22, instead of shattering, crushing, or splintering the bone 22 into fragmented pieces. This shearing action is crucial in consistently and efficiently transforming the bone 22 into the correct sized micron particles of bone tissue powder 70. Without the shearing action a large majority of the bone 22 sample can be destroyed or rendered unsuitable for medical applications. The shearing action also reduces the amount of heat produced during the processing of bone 22 into bone tissue powder 70. Therefore, the shearing action also maintains the morphogenetic proteins, which in turn preserves the osteoinductive characteristic of the bone 22.

Figure 9:
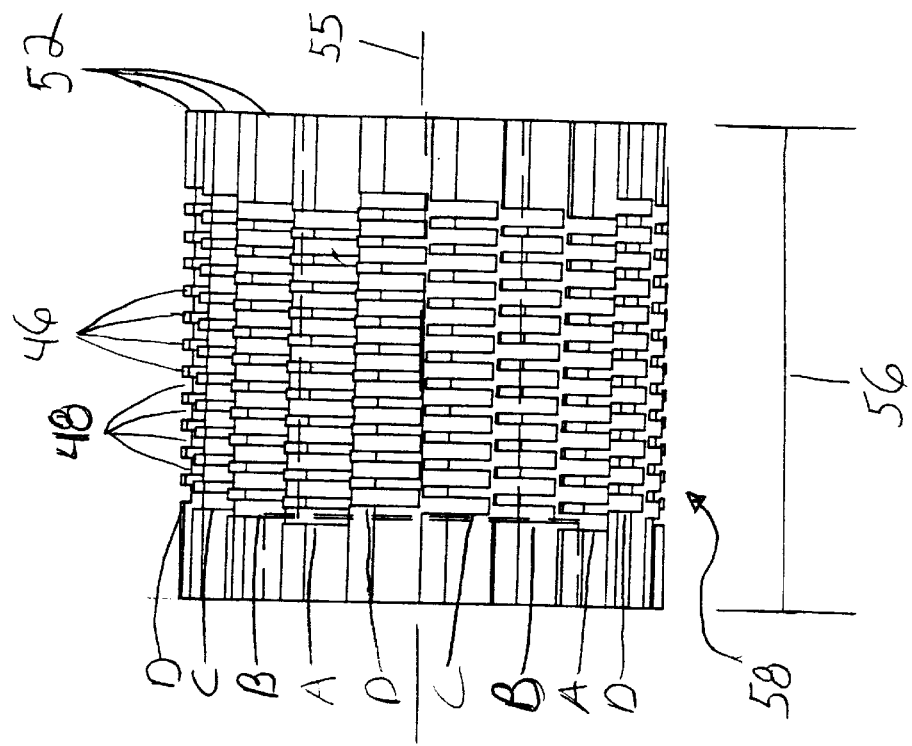
FIG. 9 is a side view of the primary cutting element showing the set of teeth positioned in offset rows along the circumference and radial length of the cutting element.
Figure 8:
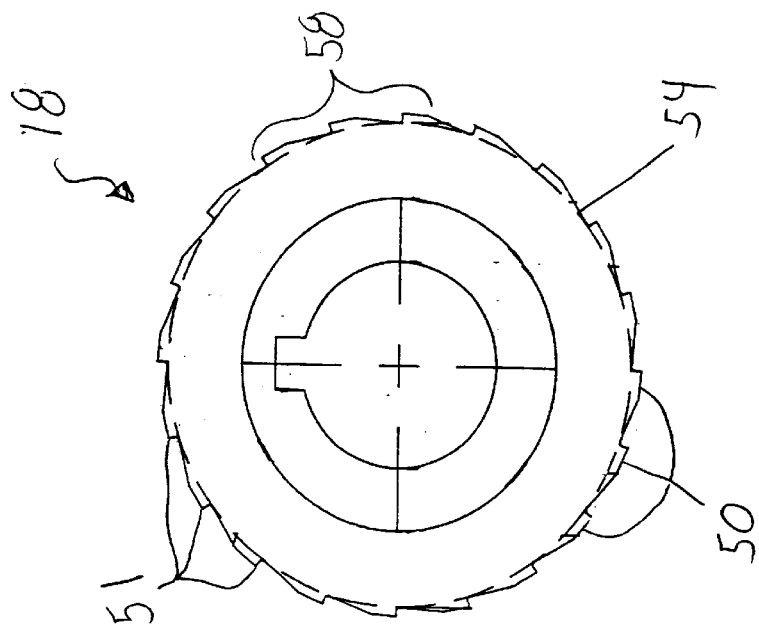
FIG. 8 is a front view of the primary cutting element.

In a preferred embodiment of the current invention, each cutting element 17 includes a circumference 74, an axis 55, an axial length 56 and a set of teeth 58 spanning the majority of the circumference 54 and the majority of the axial length 56 of the associated cutting element 17. Specifically, the set of teeth 58 of the primary cutting element 18 is positioned in offset rows 52 along the axial length 56 of the primary cutting element 18, as seen in FIG. 9. The primary cutting element 18 is designed to allow deep cuts of the bone 22. This allows for the correct size of intermediary pieces 78 to transfer into the next stage of cutting at the secondary cutting element 20.

The exact size of the intermediary pieces 78 of bone 22 and the bone tissue powder 70 are determined by the rake, shape, height, spacing, angle of teeth, and polish and depth of the flutes. This allows replacement of the cutting elements 17 to arrive at any desired particle size and shape of bone tissue powder 70.

In a preferred embodiment, primary cutting element 18 has a diameter 53 of 2.916 inches and an axial length 56 of 2.925 inches. The primary cutting element 18 contains 20 offset rows 52 in the set of teeth 58 on the primary cutting element 18. The offset rows 52 vary in starting location along the axial length 56 of the primary cutting element 18 by 0.04 inches. The offset rows 52 comprise four separate starting locations along this axial length 56 before the offset rows 52 restart their pattern. As seen in FIG. 9, the offset rows 52 start at A then stagger by 0.04 inches in three separate increments to B, C, and then D, respectively. This pattern then resets to the original starting depth of point A along the axial length 56 of the primary cutting element 18.

Each offset row 52 in the set of teeth 58 for the primary cutting element 18 comprises 11 individual teeth 46. Each individual tooth 46 in the set of teeth 58 of the primary cutting element 18 is approximately 0.062 inches wide with the space 42 between each tooth 48 approximately 0.100 inches wide. The design of the set of teeth 58 for the primary cutting element 18 provides the correct size of intermediary pieces 78 of bone 22 to the secondary cutting elements 20. The primary cutting element 18 cuts the bone 22 down to intermediary pieces 78 ranging between 650 to 950 micron sized particles. This size of intermediary pieces 78 of bone 22 is necessary to allow the correct functioning of the secondary cutting elements 20. In alternate embodiments of the bone grinding apparatus 10, the primary cutting element 18 can be replaced with an alternate primary cutting element 18 to supply intermediary pieces 78 of bone 22 to the secondary cutting elements 20 as needed.

In this preferred embodiment, the cutting tools 25 have rows of teeth 44 comprising the set of teeth 30 and 32 on each cutting tool 26 and 28, respectively. Since the first set of teeth 30 partially overlaps and alternates with the second set of teeth 32, the cutting elements 26 and 28 must be designed to facilitate this interaction. In a preferred embodiment, cutting tool 26 contains 27 rows of teeth 44 and 28 spaces 42 between successive rows of teeth 44, while cutting tool 28 contains 28 rows of teeth 44 and 27 spaces 42 between successive rows of teeth 44. For both cutting tools 25, each row of teeth is approximately 0.020 inches wide, while the space 42 between each row of teeth 44 is approximately 0.032 inches wide. Overall, the cutting elements 25 are 1.488 inches in axial length 56 and 1.400 inches in diameter.

The bone grinding apparatus 10 further comprises a bone supplying cylinder 60 engaging the grinding chamber 16 and adapted to transport the bone 22 to the cutting elements 17 at a consistent pressure. The bone supplying cylinder 60 is comprised of a guide chute 62 and a guide cylinder 64. The guide chute 62 is specifically designed to direct bone 22 to the grinding chamber 16, with assistance from a guide rod 66 and a contact plate 68.

The key result of delivering the bone 22 to the cutting elements 17 at a consistent speed and pressure is the fact that little to no heat is produced during the cutting process. The substantial reduction in the amount of heat produced during the cutting process results in the preservation of the morphogenetic proteins, which allows the bone to retain its osteoinductivity. As previously mentioned, osteoinductivity is crucial for numerous medical applications of bone tissue powder 70.

In a preferred embodiment of the invention, the bone grinding cylinder 60 is composed of low carbon, non-magnetic, 400 series stainless steel and includes a pneumatic cylinder that allows the guide cylinder 64 and guide chute 62 to deliver the bone 22 at the consistent pressure and speed. In alternate embodiments, the bone supplying cylinder 60 could utilize a hydraulic cylinder, a turbine piston, or other standard devices known in the industry for delivering consistent power without deviating from the inventive spirit disclosed by the current invention.

The use of a pneumatic powered cylinder by the bone supplying cylinder 60 provides a slow transfer of the bone 22 to the grinding chamber 16, and eventually the primary cutting element 18 and secondary cutting element 20. However, the pneumatic power provides a high degree of torque, over 71,000 inches per pound, allowing for consistent pressure applied to the bone 22 during the delivery of the bone 22 to the primary cutting element 18 and secondary cutting element 20.

Within the bone supplying cylinder 60 is guide rod 66 and contact plate 68. As seen in FIG. 3 and 4, the guide rod 66 is attached to the contact plate 68 and travels within the guide chute 62 and guide cylinder 64 of the bone supplying cylinder 60. The guide rod 66 is designed not to rotate within bone supplying cylinder 60. The contact plate 68 is the contact element that actually engages the bone 22 once the bone 22 is loaded into the guide chute 62. The contact plate 68, with assistance from the guide rod 66 transfers the bone 22 into the grinding chamber 16 where the primary and secondary cutting elements 18 and 20 can cut the bone 22 into the desired bone tissue powder 70.

The curvature of contact plate 68 corresponds to the circumference 54 of the primary cutting element 18. This correlation allows the entire supply of bone 22 to reach the primary cutting element 18 as the bone supplying cylinder 60 uses contact plate 68 to transfer the bone 22 to the grinding chamber 16.

The bone supplying cylinder 60 can be opened at the beginning of the guide chute 62 to allow entry of the bone 22. The guide cylinder 64 is attached to the guide chute 62 by two dowel pins 72 and 74. A user of the bone grinding apparatus 10 removes the dowel pin 72 and tilts the guide cylinder 64 until it rests on stop 76, as seen in FIG. 4.

When the bone supplying cylinder 60 is opened to expose the entry to the guide chute 62, the guide rod 66 and the contact plate 68 are fully retracted within the guide cylinder 64. Once the guide cylinder 64 is returned to its closed position and dowel pin 72 is reinserted into its locking location, the bone grinding apparatus 10 is turned on and guide rod 66 forces contact plate 68 to engage the bone 22 and transfer this bone 22 through the guide chute 66 into the grinding chamber 16. Once in the grinding chamber 16, the bone 22 is cut by the primary cutting element 18 into intermediary pieces 78 of bone 22. These intermediate pieces 78 of bone 22 then travel to the secondary cutting element 20 where they are then cut into bone tissue powder 70. The bone tissue powder 70 then exits the bone grinding apparatus 10 through a discharge path 80, which is located distally from the engagement of the bone supplying cylinder 60 and the grinding chamber 16 and is positioned to dispense the bone 22 as bone tissue powder 70.

In a preferred embodiment of the invention, the process of converting the human cortical bone 22 into the bone tissue powder 70 completes a full cycle in 30 to 60 seconds. The bone grinding apparatus 10 is designed to complete a full cycle of the cutting process and then return to the original starting position. The full cycle begins after the bone 22 has been loaded into the guide chute 62 and the bone grinding apparatus 10 has been turned on. The bone supplying cylinder 60 then feeds the bone 22 to the cutting elements 17. Once the entire sample of bone 22 has passed through the cutting elements 17, all cutting elements 17 continue to rotate for an additional ten to twenty cycles. This additional rotation is a self-cleaning cycle designed to purge the bone grinding apparatus 10 of any remaining bone 22 particles. Finally, the guide rod 66 and the contact plate 68 return to their initial location of being fully retracted within the guide cylinder 64.

In this embodiment, the guide chute 62 can accept up to twelve (12) inches of bone 22. Also, due to the design of the grinding chamber 16 encompassing the entire bone 22 that is to be used as a sample, there is no waste of the bone 22 as it is processed into the bone tissue 70. In fact, less than 1% of any donor bone 22 is lost.

The bone grinding apparatus 10 further comprises a sealing component 82 environmentally separating the drive mechanism 24 from the bone supplying cylinder 60, the grinding chamber 16, and the cutting elements 17. In a preferred embodiment, this sealing component 82 comprises bearings (not shown) and a wall 84, as seen in FIG. 1.

The drive section 14 is connected to the processing section 12 through a channel 86 that passes through the wall 84. Within the channel 86 are a plurality of drive shafts 87. In a preferred embodiment, each drive shaft 88, 90, and 92 is supported by a bearing (not shown) that facilitates the environmental separation of the drive mechanism 24 from the processing section 12 of the bone grinding apparatus 10. The drive mechanism 24 is housed within a stainless steel control box 94, which contains the electronic controls (not shown) for the bone grinding apparatus 10.

Surrounding the channel 86 and engaging the wall 84 is the sealing collar 96. This sealing collar 96 aids the environmental separation of the drive section 14 of the bone grinding apparatus 10 from the processing section 12 of the bone grinding apparatus 10. This ceiling collar 96 varies in distance from the control box 94 depending on the distance control box 94 is spaced from the wall 84.

Figure 10:
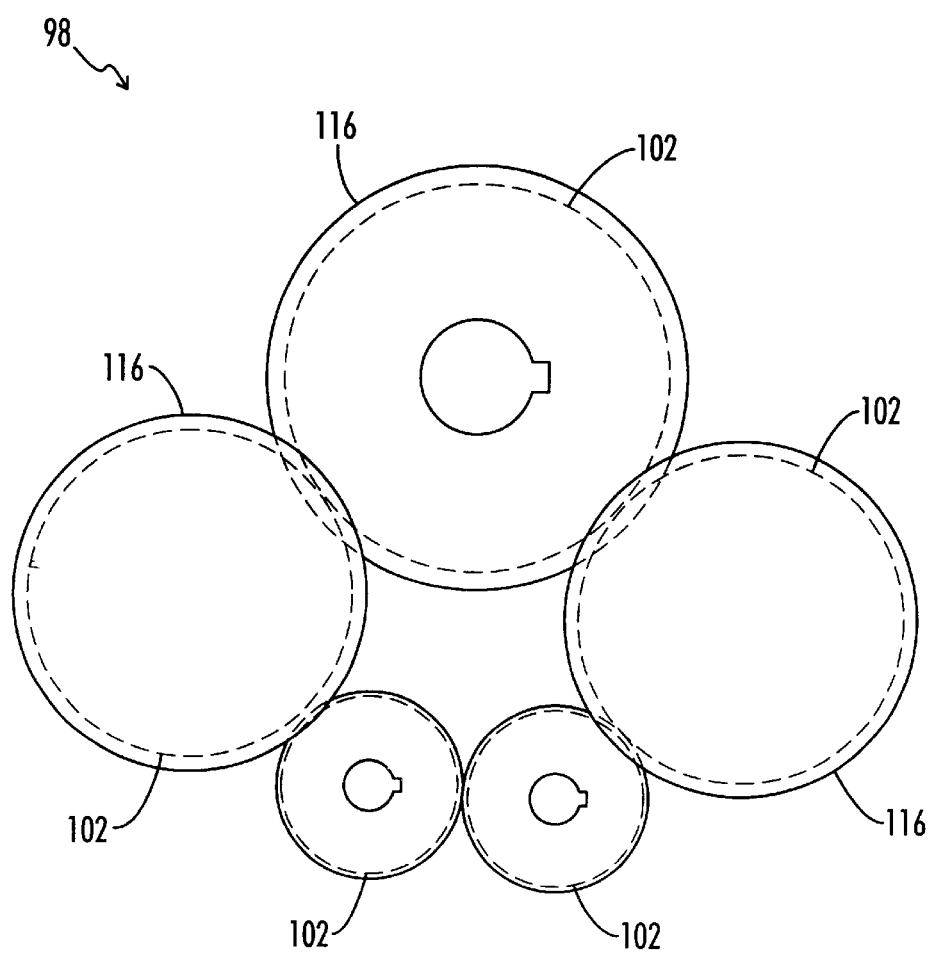
FIG. 10 is a view of the gearing system of the bone grinding apparatus. This view shows the inter-relationship between the main drive gear and the secondary gears resulting in the cutting tools of the secondary cutting element rotating in the same direction.

The drive mechanism 24 includes a gearing system 98 as seen in FIG. 10. This gearing system 98 is designed to operatively engage the plurality of cutting elements 17 and ultimately rotate each cutting element 18 and 20. The drive mechanism 24 operatively engages drive shafts 88, 90, and 92 through the gearing system 98. Specifically, each drive shaft 88, 90, and 92 engages at least one of the cutting elements 17.

The drive mechanism 24, through the use of gears 102 and clutches 116 of the gearing system 98, rotates the cutting elements 17. In a preferred embodiment, the gearing system 98 includes seven gears 102 that operate in conjunction with the drive shafts 87 and three clutches 116 to rotate the cutting elements 17. A piston style rotary actuator (not shown) is the rotation force within the drive mechanism 24.

As the a piston style rotary actuator ends it stroke, all three clutches 118, 120, and 122 release to allow the actuator to return to its initial position. During this transition, all three cutting elements 17 remain static. The length on the static period depends on the specific gearing ratios used in the gearing system 98.

For example, in this preferred embodiment the primary cutting element 18 cuts in 180 degree segments and rotates counterclockwise to an operator of the bone grinding apparatus 10 facing the processing section 12 of the bone grinding apparatus 10. The cutting tools 25 cut in 350 degree segments and also rotate in a counterclockwise direction with respect to an operator of the bone grinding apparatus 10 facing the processing section 12 of the bone grinding apparatus 10.

In a preferred embodiment of the invention, the processing section 12 of the bone grinding apparatus 10 is attached to a wall 84 by a wall plate 100. The wall plate 100 includes mounting studs (not shown) with which the processing section 12 is attached to the wall 84. The wall plate 100 also includes 3 proximately switches (not shown) which provide safety features for the bone grinding apparatus 10. If any of the proximity switches are not in connection, the bone grinding apparatus 10 will not operate. The proximity switches are located near the connection of the guide shut 62 and guide cylinder 64, and near the connection of the drive shafts 87 and the cutting elements 17.

In this preferred embodiment, the processing section 12 of the bone grinding apparatus 10 has a compressed air filtration system (not shown) operating between 60 psi to 160 psi.

This filtration system removes impurities at a level of 0.1 microns, which is enough to filter out various viruses. Also, bone grinding apparatus 10 is designed for the entire processing section 12 to be removed. This allows a second processing section 12 to be installed in its place in order to facilitate continued operation of the bone grinding apparatus 10.

The present invention includes a method for grinding bone 22. The method comprises providing a sequentially arranged plurality of cutting tools 25. The method teaches rotating a first cutting 26 and a second cutting tool 28 in the same direction 40, thereby creating a shearing action between the first cutting tool 26 and the second cutting tool 28. The method then teaches supplying bone 22 to the cutting tools 26 and 28.

The method further includes environmentally separating the cutting tools 26 and 28 from a drive mechanism 24 which is operatively engaging the cutting tools 26 and 28 and it is adapted to rotate the cutting tools 26 and 28. In a preferred embodiment this separation occurs through the usage of a wall 84 and bearings (not shown).

The method further includes initially cutting the bone 22 before the first cutting tool 26 and the second cutting tool 28 cut the bone 22. The method further includes supplying the bone 22 to the plurality of cutting tools 27 at a constant pressure.

Thus, it is seen that the apparatus of the present invention readily achieves the ends and advantages mentioned as well as those inherent therein. While certain preferred embodiments of the invention have been illustrated and described for purposes of the present disclosure, numerous changes in the arrangement and construction of parts may be made by those skilled in the art, which changes are encompassed within the scope and spirit of the present invention as defined by the appended claims.

What is claimed is:

1. A bone grinding apparatus, comprising
   a grinding chamber;
   primary and secondary cutting elements positioned within the grinding chamber to sequentially perform primary and secondary cutting operations on the bone;
   a drive mechanism operatively engaging the primary and secondary cutting elements;
   wherein the secondary cutting element comprises:
      a first cutting tool including a first set of teeth;
      a second cutting tool including a second set of teeth; and
      the first and second cutting tools are positioned to define a cutting zone between the first set of teeth and the second set of teeth; and
   wherein the first cutting tool and second cutting tool are positioned in an opposed relationship within the grinding chamber and wherein the drive mechanism is adapted to move the first set of teeth in a first direction through the cutting zone and to move the second set of teeth in an opposite direction through the cutting zone, whereby concurrent movement of the first set of teeth and the second set of teeth will apply shear forces to the bone located in the cutting zone.

2. The apparatus of claim 1, wherein the first set of teeth is positioned within the cutting zone to alternate with and partially overlap the second set of teeth.

3. The apparatus of claim 1, wherein each cutting element includes a circumference, an axial length, and a set of teeth spanning a majority of the circumference and a majority of the axial length of the associated cutting element.

4. The apparatus of claim 3, wherein each tooth in each set of teeth includes:
   a tooth face extending radially from the circumference of the cutting element; and
   a top surface positioned substantially perpendicular to the tooth face to create a cutting edge.

5. The apparatus of claim 3, wherein the set of teeth of the primary cutting element is positioned in offset rows along the axial length of the primary cutting element.

6. The apparatus of claim 1, further comprising:
   a bone supplying cylinder engaging the grinding chamber and adapted to transport the bone to the cutting elements at a consistent pressure; and
   a discharge path located distally from the engagement of the bone supplying cylinder and the grinding chamber and positioned to dispense cut bone.

7. The apparatus of claim 6, wherein the bone supplying cylinder includes a guide chute engaging the grinding chamber and positioned to direct the bone to the grinding chamber.

8. The apparatus of claim 1, further comprising a sealing component positioned to environmentally separate the drive mechanism from the grinding chamber and the cutting elements.

9. The apparatus of claim 1, further comprising:
   a gearing system operatively engaging each cutting element and the driving mechanism, the gearing system adapted to control the rotational direction and speed of each cutting element; and
   a plurality of drive shafts, each drive shaft operatively engaging the gearing system and one of the cutting elements.

10. A bone grinding apparatus, comprising
    a grinding chamber;
    primary and secondary cutting elements positioned within the grinding chamber to sequentially perform primary and secondary cutting operations on the bone;
    a drive mechanism operatively engaging the primary and secondary cutting elements;
    wherein the secondary cutting element comprises:
       a first cutting tool including a first set of teeth;
       a second cutting tool including a second set of teeth; and
       the first and second cutting tools are positioned to define a cutting zone between the first set of teeth and the second set of teeth; and
    wherein the first cutting tool and second cutting tool are positioned in an opposed relationship within the grinding chamber and wherein the drive mechanism is adapted to concurrently rotate the first cutting tool and the second cutting tool in the same direction, whereby the first set of teeth and the second set of teeth apply shear forces to the bone located in the cutting zone.

11. The apparatus of claim 10, wherein the first set of teeth is positioned within the cutting zone to alternate with and partially overlap the second set of teeth.

12. The apparatus of claim 10, wherein each cutting element includes a circumference, an axial length, and a set of teeth spanning a majority of the circumference and a majority of the axial length of the associated cutting element.

13. The apparatus of claim 12, wherein each tooth in each set of teeth includes:
    a tooth face extending radially from the circumference of the cutting element; and a top surface positioned substantially perpendicular to the tooth face to create a cutting edge.

14. The apparatus of claim 12, wherein the set of teeth of the primary cutting element is positioned in offset rows along the axial length of the primary cutting element.

15. The apparatus of claim 10, further comprising:
a bone supplying cylinder engaging the grinding chamber and adapted to transport the bone to the cutting elements at a consistent pressure; and
a discharge path located distally from the engagement of the bone supplying cylinder and the grinding chamber and positioned to dispense cut bone.

16. The apparatus of claim 15, wherein the bone supplying cylinder includes a guide chute engaging the grinding chamber and positioned to direct the bone to the grinding chamber.

17. The apparatus of claim 10, further comprising a sealing component positioned to environmentally separate the drive mechanism from the grinding chamber and the cutting elements.

18. The apparatus of claim 10, further comprising:
a gearing system operatively engaging each cutting element and the driving mechanism, the gearing system adapted to control the rotational direction and speed of each cutting element; and
a plurality of drive shafts, each drive shaft operatively engaging the gearing system and one of the cutting elements.

19. An apparatus for grinding bone comprising:
a grinding chamber;
a first cutting element positioned within the grinding chamber to initially cut the bone;
a second cutting element positioned within the grinding chamber, the second cutting element including a first cutting tool and a second cutting tool positioned in an opposed relationship to define a cutting zone between the cutting tools;
a drive mechanism operatively engaging each cutting element and adapted to concurrently rotate each cutting element; and
wherein the first cutting element includes:
a circumference;
an axial length; and
a set of teeth spanning a majority of the circumference of the first cutting element and positioned in offset rows along a majority of the axial length of the first cutting element.

20. An apparatus for grinding bone comprising:
a grinding chamber;
a first cutting element positioned within the grinding chamber to initially cut the bone;
a second cutting element positioned within the grinding chamber, the second cutting element including a first cutting tool and a second cutting tool positioned in an opposed relationship to define a cutting zone between the cutting tools;
a drive mechanism operatively engaging each cutting element and adapted to concurrently rotate each cutting element; and
wherein the first cutting tool includes a first set of teeth and the second cutting tool includes a second set of teeth and wherein the drive mechanism is adapted to move the first set of teeth in a first direction through the cutting zone and to move the second set of teeth in an opposite direction through the cutting zone, whereby concurrent movement of the first set of teeth and the second set of teeth will apply shear forces to the bone located in the cutting zone.

21. An apparatus for grinding bone comprising:
a grinding chamber;
a first cutting element positioned within the grinding chamber to initially cut the bone;
a second cutting element positioned within the grinding chamber, the second cutting element including a first cutting tool and a second cutting tool positioned in an opposed relationship to define a cutting zone between the cutting tools;
a drive mechanism operatively engaging each cutting element and adapted to concurrently rotate each cutting element; and
wherein the first cutting tool includes a first set of teeth and the second cutting tool includes a second set of teeth and wherein the drive mechanism is adapted to concurrently rotate the first cutting tool and the second cutting tool in the same direction, whereby the first set of teeth and second set of teeth apply shear forces to the bone located in the cutting zone.

22. An apparatus for grinding bone comprising:
a grinding chamber;
a first cutting element positioned within the grinding chamber to initially cut the bone;
a second cutting element positioned within the grinding chamber, the second cutting element including a first cutting tool and a second cutting tool positioned in an opposed relationship to define a cutting zone between the cutting tools;
a drive mechanism operatively engaging each cutting element and adapted to concurrently rotate each cutting element; and
wherein each cutting tool includes a circumference, an axial length, and a set of teeth spanning a majority of the circumference along the majority of the axial length of the cutting tool.

23. The apparatus of claim 22, wherein each tooth in each set of teeth includes:
a tooth face extending radially from the circumference of the cutting tool; and
a top surface positioned substantially perpendicular to the tooth face to create a cutting edge.

24. The apparatus of claim 22, wherein the first cutting tool includes a first set of teeth and the second cutting tool includes a second set of teeth, whereby the first set of teeth is positioned within the cutting zone to alternate with and partially overlap the second set of teeth.

25. The apparatus of claim 22, further comprising a sealing component positioned to environmentally separate the drive mechanism from the grinding chamber and each cutting element.

26. The apparatus of claim 22, further comprising a bone supplying cylinder engaging the grinding chamber and adapted to transport the bone to the grinding chamber at a constant pressure.

27. A bone grinding apparatus, comprising:
a plurality of cutting elements;
a grinding chamber encompassing the cutting elements;
a drive mechanism operatively engaging the cutting elements and adapted to rotate the cutting elements;
a bone supplying cylinder operatively engaging the grinding chamber and adapted to supply bone to the cutting elements at a constant pressure;

a sealing component operatively engaging the drive mechanism and positioned to environmentally separate the drive mechanism from the cutting elements, the grinding chamber, and the bone supplying cylinder;

wherein the plurality of cutting elements further comprises:
 a primary cutting element positioned to initially engage the bone; and
 a secondary cutting element including a first cutting tool and a second cutting tool, the cutting tools positioned to define a cutting zone within the grinding chamber and to concurrently engage the bone in the cutting zone; and wherein the drive mechanism operatively engages the cutting elements and wherein the drive mechanism is adapted to rotate the first cutting tool and the second cutting tool in the same direction, thereby creating a shearing effect between the first cutting tool and second cutting tool in the cutting zone.

28. A bone grinding apparatus, comprising:

a plurality of cutting elements;

a grinding chamber encompassing the cutting elements;

a drive mechanism operatively engaging the cutting elements and adapted to rotate the cutting elements;

a bone supplying cylinder operatively engaging the grinding chamber and adapted to supply bone to the cutting elements at a constant pressure;

a sealing component operatively engaging the drive mechanism and positioned to environmentally separate the drive mechanism from the cutting elements, the grinding chamber, and the bone supplying cylinder; and wherein the bone supplying cylinder includes:
 a guide chute engaging the grinding chamber;
 a guide rod positioned within the guide chute; and
 a contact plate engaging the guide rod, the contact plate positioned to transport bone through the guide chute to the cutting elements at a constant pressure.

29. The apparatus of claim 28, wherein the drive mechanism further comprises a plurality of drive shafts and the sealing component includes a wall operatively engaging the drive shafts and environmentally separating the drive mechanism from the grinding chamber and the cutting elements.

30. A method for grinding bone, the method comprising:
 (a) providing a proximately arranged plurality of cutting tools;
 (b) rotating a first cutting tool and a second cutting tool in the same direction, thereby creating a shearing action between the first cutting tool and the second cutting tool; and
 (c) supplying bone to the cutting tools.

31. The method of claim 30, wherein in step (b) further includes rotating the cutting tools with a drive mechanism and environmentally separating the cutting tools from the drive mechanism.

32. The method of claim 30, wherein step (c) further includes cutting the bone before the cutting tools receive the bone.

33. The method of claim 30, wherein step (c) further includes supplying the bone to the cutting tools at a constant pressure.

* * * * *